US012778669B2

(12) United States Patent
Rollins et al.

(10) Patent No.: US 12,778,669 B2
(45) Date of Patent: Nov. 3, 2026

(54) INTEGRATED IMAGING ABLATION CATHETER

(71) Applicant: CASE WESTERN RESERVE UNIVERSITY, Cleveland, OH (US)

(72) Inventors: Andrew M. Rollins, Cleveland, OH (US); Xiaowei Zhao, Cleveland, OH (US); Reza Mohammadpour, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 870 days.

(21) Appl. No.: 17/552,448

(22) Filed: Dec. 16, 2021

(65) Prior Publication Data

US 2022/0192743 A1 Jun. 23, 2022

Related U.S. Application Data

(60) Provisional application No. 63/127,560, filed on Dec. 18, 2020.

(51) Int. Cl.

| | |
|---|---|
| ***A61B 18/14*** | (2006.01) |
| *A61B 5/00* | (2006.01) |
| *A61B 18/00* | (2006.01) |

(52) U.S. Cl.

CPC ........ *A61B 18/1492* (2013.01); *A61B 5/0066* (2013.01); *A61B 2018/00577* (2013.01);

(Continued)

(58) Field of Classification Search

CPC ...... A61B 18/1492; A61B 2018/00577; A61B 2018/00708; A61B 2018/00821;

(Continued)

(56) References Cited

U.S. PATENT DOCUMENTS 6,208,415 B1 3/2001 De Boer et al.
6,241,722 B1 6/2001 Dobak et al.

(Continued)

OTHER PUBLICATIONS

Xiaowei Zhao, et al.; "Intracardiac radiofrequency ablation in living swine guided by polarization-sensitive optical coherence tomography"; Journal Article—Journal of Biomedical Optics, vol. 25, Issue: 5, May 8, 2020; 11 pgs.

(Continued)

*Primary Examiner* — Beverly M Flanagan
*Assistant Examiner* — Abigail M Ziegler
(74) *Attorney, Agent, or Firm* — Tarolli, Sundheim, Covell & Tummino LLP

(57) ABSTRACT

A described example provides an ablation catheter including an elongate tubular body having spaced apart proximal and distal ends and a lumen extending through the elongate tubular body. An ablation electrode extends from the distal end of the elongate tubular body to terminate in a distal end thereof. An elongate optical imaging probe extends through the lumen of the elongate tubular body and terminates in a distal end that is spaced a distance from the distal end of the ablation electrode. A flexible tubing extends over a length of the probe and configured to permit at least rotational movement of the probe within the flexible tubing. A distal end portion of the flexible tubing can be held at an axial position relative to the elongate tubular body to fix the distance between the distal end of the probe and the distal end of the ablation electrode.

22 Claims, 5 Drawing Sheets

(52) U.S. Cl.
CPC ............... *A61B 2018/00613* (2013.01); *A61B 2018/00708* (2013.01); *A61B 2018/00821* (2013.01); *A61B 2018/00982* (2013.01); *A61B 2018/1467* (2013.01)

(58) Field of Classification Search
CPC .. A61B 2018/00982; A61B 2018/1467; A61B 2018/00142; A61B 2018/00791
See application file for complete search history.

(56) References Cited

U.S. PATENT DOCUMENTS

| | | | | |
|---|---|---|---|---|
| 6,498,652 | B1 | 12/2002 | Varshneya et al. | |
| 6,595,991 | B2 | 7/2003 | Toellner et al. | |
| 6,817,999 | B2 | 11/2004 | Berube et al. | |
| 6,961,123 | B1 | 11/2005 | Wang et al. | |
| 7,102,756 | B2 | 9/2006 | Izatt et al. | |
| 7,519,096 | B2 | 4/2009 | Bouma et al. | |
| 7,527,625 | B2 | 5/2009 | Knight et al. | |
| 7,538,859 | B2 | 5/2009 | Tearney et al. | |
| 7,787,129 | B2 | 8/2010 | Zysk et al. | |
| 7,869,663 | B2 | 1/2011 | Buckland et al. | |
| 8,050,747 | B2 | 11/2011 | Tearney et al. | |
| 8,059,274 | B2 | 11/2011 | Splinter | |
| 8,301,027 | B2 | 10/2012 | Shaw et al. | |
| 8,724,864 | B2 | 5/2014 | Persson et al. | |
| 9,089,331 | B2 | 7/2015 | Rollins et al. | |
| 9,622,706 | B2 | 4/2017 | Dick et al. | |
| 9,883,901 | B2 | 2/2018 | Rollins et al. | |
| 9,885,557 | B2 | 2/2018 | Wang et al. | |
| 10,085,798 | B2 | 10/2018 | Cao et al. | |
| 10,779,904 | B2 * | 9/2020 | Ransbury | A61B 90/30 |
| 2003/0120142 | A1 | 6/2003 | Dubuc et al. | |
| 2003/0208252 | A1 | 11/2003 | O&apos et al. | |
| 2005/0251116 | A1 | 11/2005 | Steinke et al. | |
| 2006/0030844 | A1 * | 2/2006 | Knight | A61B 18/1492 606/41 |
| 2007/0270792 | A1 | 11/2007 | Hennemann et al. | |
| 2007/0287998 | A1 * | 12/2007 | Sharareh | A61B 18/1492 606/41 |
| 2008/0024788 | A1 | 1/2008 | Shimizu et al. | |
| 2008/0089641 | A1 | 4/2008 | Feldchtein | |
| 2009/0214615 | A1 | 8/2009 | Zhao | |
| 2009/0221920 | A1 | 9/2009 | Boppart et al. | |
| 2009/0306520 | A1 | 12/2009 | Schmitt et al. | |
| 2010/0041986 | A1 | 2/2010 | Nguyen et al. | |
| 2010/0185054 | A1 * | 7/2010 | Ramzipoor | A61B 1/00135 600/114 |
| 2011/0009741 | A1 | 1/2011 | Matthews et al. | |
| 2011/0144503 | A1 | 6/2011 | Debreczeny et al. | |
| 2011/0267583 | A1 | 11/2011 | Hayashi | |
| 2013/0072928 | A1 | 3/2013 | Schaer | |
| 2013/0137980 | A1 * | 5/2013 | Waters | A61B 18/18 600/439 |
| 2014/0163360 | A1 * | 6/2014 | Stevens-Wright | A61B 5/0036 600/104 |
| 2015/0202002 | A1 | 7/2015 | Rollins et al. | |
| 2015/0209105 | A1 | 7/2015 | Margallo Balbás et al. | |
| 2017/0027639 | A1 | 2/2017 | Margallo Balbás et al. | |
| 2017/0156705 | A1 * | 6/2017 | Galluzzo | A61B 8/085 |
| 2018/0156596 | A1 | 6/2018 | Wang et al. | |
| 2018/0271491 | A1 * | 9/2018 | Flanagan | A61B 8/5215 |
| 2021/0212755 | A1 * | 7/2021 | Jimenez | A61B 5/6856 |

OTHER PUBLICATIONS

David Herranz, et al.; "Percutaneous RF Ablation Guided by Polarization-sensitive Optical Coherence Reflectometry in an Integrated Catheter: Experimental Evaluation of the Procedure"; The Journal of Innovations in Cardiac Rhythm Management, 6 (2015), 2086-2091; DOI: 10.19102/icrm.2014.060803.

Kiaoyong Fu, et al., "Fiber-optic catheter-based polarization-sensitive OCT for radio-frequency ablation monitoring," HHS Public Access, Author Manuscript; Opt. Lett. Sep. 1, 2014; 39 (17): 5066-5069.

Kiaowei Zhao, et al.; "Polarization-sensitive optical coherence tomography monitoring of percutaneous radiofrequency ablation in left atrium of living swine"; Sci Rep 11, 24330 (2021); www.nature.com/scientificreports; https://doi.org/10.1038/s41598-021-03724-8.

B. Hyle Park, et al.; "In vivo burn depth determination by high-speed fiber-based polarization sensitive optical coherence tomography"; Journal of Biomedical Optics 6(4), 474-479 (Oct. 2001).

Hugh Calkins, et al.; "2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design"; HRS/EHRA/ECAS Expert Consensus Statement; Europace (2012) 14, 528-606; doi:10.1093/europace/eus027.

Bernhard Baumann, et al.; "Swept source / Fourier domain polarization sensitive optical coherence tomography with a passive polarization delay unit"; Optical Society of America; Opt. Express 20, 10229-10241 (2012).

Melanie Gunawardene, et al.; "A novel assessment of local impedance during catheter ablation: initial experience in humans comparing local and generator measurements"; ESC European Society of Cardiology; Europace (2019) 21, i34-i42; doi:10.1093/europace/euy273.

Pierre Jaïs, et al.; "Ablation therapy for atrial fibrillation (AF): Past, present and future", Cardiovascular Research, vol. 54, Issue 2, May 2002, pp. 337-346, https://doi.org/10.1016/S0008-6363(02)00263-8.

Richard B. Schuessler, PhD, et al.; "Animal studies of epicardial atrial ablation"; Elsevier Heart Rhythm vol. 6, Issue 12, Supplement, Dec. 2009, pp. S41-S45.

Timm Dickfeld, MD, PhD, et al.; "Characterization of Radiofrequency Ablation Lesions With Gadolinium-Enhanced Cardiovascular Magnetic Resonance Imaging"; Published by Elsevier Inc.; Journal of the American College of Cardiology; vol. 47, No. 2, 2006; ISSN 0735-1097/06; 9 pgs.; doi: 10.1016/j.jacc.2005.07.070.

Hans Kottkamp, MD, et al.; "Catheter Ablation of Atrial Fibrillation"; Published by Elsevier Inc.; Journal of the American College of Cardiology; vol. 65, No. 2, 2015; ISSN 0735-1097; 11 pgs.; http://dx.doi.org/10.1016/j.jacc.2014.10.034.

Alvaro Alonso, et al.; "Atrial Fibrillation, Cognitive Decline and Dementia"; Access at www.ECRjournal.com; Radcliffe Cardiology; Jul. 31, 2016; 5 pgs.

Christopher R.C.Wynhdham, MD, FRACP, FACC; Atrial Fibrillation the Most Common Arrhythmia; Cardiac Arrhythmias; Texas Heart Institute Journal; Feb. 5, 2000; 11 pgs.

Sharon Thomsen, et al.; "Changes in Birefringence as Markers of Thermal Damage in Tissues"; IEEE Transactions on Biomedical Engineering. vol. 36 No. 12, Dec. 1989; 6 pgs.

Hiroshi Nakagawa, MD, PhD, et al.; "Comparison of In Vivo Tissue Temperature Profile and Lesion Geometry for Radiofrequency Ablation With a Saline-Irrigated Electrode Versus Temperature Control in a Canine Thigh Muscle Preparation"; Circulation circ.ahajournals.org; Circulation. 1995,91:2264-2273 American Heart Association, Inc.; 13 pgs. doi: 10.1161/ 01.CIR.91.8.2264.

Carlo Pappone, MD, PhD, et al.; "Circumferential Radiofrequency Ablation of Pulmonary Vein Ostia—A New Anatomic Approach for Curing Atrial Fibrillation"; American Heart Association, Inc.—Circulation; downloaded from http://ahajournals.org on Oct. 19, 2020; 10 pgs.

Brigitta Holmbom, et al; "Comparison of triphenyltetrazolium chloride (TTC) staining versus detection of fibronectin in experimental myocardial infarction"; Histochemistry Springer-Verlag 1993 99:265-275; Nov. 30, 1992.

Kara Garrott, PhD, et al.; "Combined local impedance and contact force for radiofrequency ablation assessment"; Heart Rhythm Society (Heart Rhythm 2020;17:1371-1380).

Harish Doppalapudi, MD, et al.; "Complications during catheter ablation of atrial fibrillation: Identification and prevention"; Heart Rhythm Society; 2009; 8 pgs.; doi:10.1016/j.hrthm.2009.07.025.

(56) References Cited

OTHER PUBLICATIONS

Martin Villiger, et al.; "Deep tissue volume imaging of birefringence through fibre-optic needle probes for the delineation of breast tumour"; Scientific Reports; Jul. 10, 2016; 11 pgs.
Derek H. Tang, et al.; "Economic Burden and Disparities in Healthcare Resource use Among Adult Patients with Cardiac Arrhythmia"; Springer International Publishing Switzerland; Appl. Health Econ Health Policy (2014) 12:59-71; Dec. 6, 2013; 13 pgs.
Matthew D. Olson, et al.; "Effect of catheter movement and contact during application of radiofrequency energy on ablation lesion characteristics"; J. Interv Card Electrophysiol (2013) 38:123-129; Sep. 11, 2013; 7 pgs.
Feifan Ouyang, MD, et al.; "Electrophysiological Findings During Ablation of Persistent Atrial Fibrillation With Electroanatomic Mapping and Double Lasso Catheter Technique"; Arrhythmia/Electrophysiology; Circulation; Downloaded from http://ahajournals.org on Mar. 18, 2019; 11 pgs.; DOI: 10.1161/CIRCULATIONAHA.105.561183.
Çag? La Özsoy, et al.; "Endocardial irrigated catheter for volumetric optoacoustic mapping of radio-frequency ablation lesion progression"; Optics Letters vol. 44, No. 23, Dec. 1, 2019; 4 pgs.
Wei Kang, et al.; "Endoscopically guided spectral-domain OCT with double-balloon catheters"; Optical Society of America; Optics Express; Aug. 2, 2010; vol. 18, No. 16; 9 pgs.
Dariush Mozaffarian, MD, DrPH, FAHA, et al.; "AHA Statistical Update—Executive Summary: Heart Disease and Stroke Statistics—2016 Update—A Report fromthe American Heart Association"; Circulation; downloaded from http://ahajournals.org on Nov. 6, 2020; 8 pgs.
Rajinder P. Singh-Moon, et al.; "Feasibility of near-infrared spectroscopy as a tool for anatomical mapping of the human epicardium"; Biomedical Optics Express vol. 11, No. 8; Aug. 1, 2020; 11 pgs.
Christine P. Fleming, et al.; "First in vivo Real-Time Imaging of Endocardial Radiofrequency Ablation by Optical Coherence Tomography: Implications on Safety and The Birth of "Electro-structural" Substrate-Guided Ablation"; Innovative Techniques Section; The Journal of Innovations in Cardiac Rhythm Management, Mar. 2011; 3 pgs.
Daniel Scherr, MD, et al.; "Five-Year Outcome of Catheter Ablation of Persistent Atrial Fibrillation Using Termination of Atrial Fibrillation as a Procedural Endpoint"; Original Article; http://ahajournals.org on Apr. 15, 2019; 7 pgs.
Stephen A. Boppart, Ph.D., et al.; "High-Resolution Optical Coherence Tomography-Guided Laser Ablation of Surgical Tissue"; Journal of Surgical Research 82, Sep. 17, 1998; 10 pgs.
Peter Whittaker, PhD., et al.; "Histologic Signatures of Thermal Injury: Applications in Transmyocardial Laser Revascularization and Radiofrequency Ablation"; Lasers in Surgery and Medicine 27m Apr. 11, 2000; 14 pgs.
Christine P. Fleming, et al.; "In vitro characterization of cardiac radiofrequency ablation lesions using optical coherence tomography"; Optical Society of America; Optics Express vol. 18, No. 3, Feb. 1, 2010; 14 pgs.
Nicholas Dana, BSc, et al.; "In vitro photoacoustic visualization of myocardial ablation lesions"; Heart Rhythm Society: (2014); 8 pgs.; http://dx.doi.org/10/1016/j.hrthm.2013.09.071.
Guillermo J. Teamney, et al.; "In Vivo Endoscopic Optical Biopsy with Optical Coherence Tomography"; www.sciencemag.org, Science vol. 276 Jun. 27, 1997; 4 pgs.
Hui Wang, et al.; "In vivo intracardiac optical coherence tomography imaging through percutaneous access: toward mage-guided radio-frequency ablation"; Journal of Biomedical Optics; SPIEDigital-Library.org/jbo; Nov. 28, 2016; 4 pgs.
Marius Bohnen, BSc, et al.; "Incidence and predictors of major complications from contemporary catheter ablation to treat cardiac arrhythmias"; Heart Rhythm Society; 2011; 6 pgs.; doi:10.1016/j.hthm.2011.05.017.
Johannes Rebling, et al.; "Integrated catheter for simultaneous radio frequency ablation and optoacoustic monitoring of esion progression"; Optics Letters; vol. 43, No. 8; Apr. 15, 2018; 4 pgs.
Xiaowei Zhao, et al.; "Integrated RFA/PSOCT catheter for real-time guidance of cardiac radio-frequency ablation"; Biomedical Optics Express; vol. 9, No. 12, Dec. 1, 2018; 12 pgs.
Boris A. Hoffman, et al.; "Interactive real-time mapping and catheter ablation of the cavotricuspid isthmus guided by magnetic resonance imaging in a porcine model"; Clinical Research, Arrhythmia/electrophysiology; European Heart Journal, 31; 7 pgs. doi:10.1093/eurheartj/ehp460.
Richard Kobza, MD, et al.; "Late recurrent arrhythmias after ablation of atrial fibrillation: Incidence, mechanisms, and treatment"; Heart Rhythm Society; (2004); 8 pgs. doi: 10.1016/j.hrthm.2004/08.009.
Roy Beinart, M.D., et al.; "Left Atrial Wall Thickness Variability Measured by CT Scans in Patients Undergoing Pulmonary Vein Isolation"; Apr. 13, 2011; 5 pgs.; doi: 10.1111/j.1540-8167.2011.02100.x.
Jing-Yi Sun, et al.; "Left Atrium Wall-mapping Application for Wall Thickness Visualisation"; Scientific Reports; www.nature.coim/scientificreports; Mar. 8, 2018; 13 pgs. doi: 10.1038/s41598-018-22089-z.
Gareth J. Wynn, et al.; "Long-term outcomes after ablation of persistent atrial fibrillation: an observational study over 6 years"; Arrhythmias and Sudden Death, Openheart; CrossMark; May 1, 2016; 9 pgs.; doi:10.1136/openhrt-2015-000394.
V. Ozenne, et al.; "Magnetic Resonance Imaging guided cardiac radiofrequency ablation"; ScienceDirect (www.sciencedirect.com); EM consulte—Elsevier Masson France; ANR TESCSAN 2015; Feb. 18, 2015; 6 pgs.
Christoph K. Hitzenberger, et al.; "Measurement and imaging of birefringence and optic axis orientation by phase resolved polarization sensitive optical coherence tomography"; Optics Express vol. 9, No. 13; Dec. 17, 2001; 11 pgs.
David E. Haines, MD, et al.; Original Article—"Microembolism and Catheter Ablation I—A Comparison of Irrigated Radiofrequency and Multielectrode-phased Radiofrequency Catheter Ablation of Pulmonary Vein Ostia"; Circ Arrhythm Electrophysiol (http://ahajournals.org Aug. 24, 2020; 7 pgs.
David E. Haines, et al.; Original Article "Near-Field Ultrasound Imaging During Radiofrequency Catheter Ablation Tissue Thickness and Epicardial Wall Visualization and Assessment of Radiofrequency Ablation Lesion Formation and Depth"; Circ Arrhythm Electrophsiol Dec. 2017; 12 pgs.; DOI:10.1161/CIRCEP.117.05295.
Rajinder P. Singh-Moon, et al.; "Near-infrared spectroscopy integrated catheter for characterization of myocardial tissues: preliminary demonstrations to radiofrequency ablation therapy for atrial fibrillation"; Biomedical Optics Express vol. 6, No. 7; Jul. 1, 2015; 18 pgs., DOI:10.1364/BOE.6.002494.
D. Herranz, et al.; "Novel catheter enabling simultaneous radiofrequency ablation and optical coherence reflectometry"; Biomedical Optics Express, vol. 6, No. 9; Sep. 1, 2015; 8 pgs.; DOI:10/1364/BOE.6.003268.

* cited by examiner

INTEGRATED IMAGING ABLATION CATHETER

CROSS-REFERENCE TO RELATED APPLICATION

This application claims the benefit of priority to U.S. Provisional Application No. 63/127,560, filed Dec. 18, 2020, which is incorporated herein by reference in its entirety.

GOVERNMENT FUNDING

This invention was made with government support under Grant Nos. R01HL149369 and UH54HL119810 awarded by the National Institutes of Health. The United States government has certain rights in the invention.

TECHNICAL FIELD

The present disclosure relates to integrating imaging in an ablation catheter.

BACKGROUND

Atrial fibrillation (AF) is a common sustained arrhythmia throughout much of the world. Because most AF is initiated by aberrant electrical activity originating within the pulmonary veins (PVs), PV isolation (PVI) using radiofrequency ablation (RFA) has become a common curative procedure to treat AF. During PVI, lines of RFA lesions are created around the PVs to electrically isolate them from the left atrium (LA). The efficacy of this procedure greatly relies on transmurality of individual lesions. However, current PVI lesion formation is guided only with indirect information (e.g. temperature, impedance, contact force), which may lead to non-transmural lesions, and contribute to AF recurrence. Therefore, direct lesion transmurality feedback to guide PVI procedures may potentially improve its efficacy.

SUMMARY

In an example, an ablation catheter includes an elongate tubular body having spaced apart proximal and distal ends and a lumen extending through the elongate tubular body. An ablation electrode extends from the distal end of the elongate tubular body to terminate in a distal end thereof. An elongate optical imaging probe extends through the lumen of the elongate tubular body and terminates in a distal end that is spaced a distance from the distal end of the ablation electrode. A flexible tubing extends over a length of the probe and configured to permit at least rotational movement of the probe within the flexible tubing. A distal end portion of the flexible tubing can be held at an axial position relative to the elongate tubular body to fix the distance between the distal end of the probe and the distal end of the ablation electrode.

A system can include a catheter, a pulse generator and a controller. The catheter includes an elongate tubular body having spaced apart proximal and distal ends and a lumen extending through the elongate tubular body. The catheter also includes an ablation electrode extending from the distal end of the elongate tubular body to terminate in a respective distal end of the electrode. The catheter also includes an elongate optical imaging probe extending through the lumen. The catheter also includes flexible tubing extending over a length of the probe and configured to permit at least rotational movement of the probe within the flexible tubing, in which a distal end portion of the flexible tubing being held at an axial position relative to the elongate tubular body to fix the distance between the distal end of the probe and the distal end of the ablation electrode. The controller is configured to control the pulse generator to supply electrical energy to the electrode to implement ablation.

DETAILED DESCRIPTION

Figure 1:
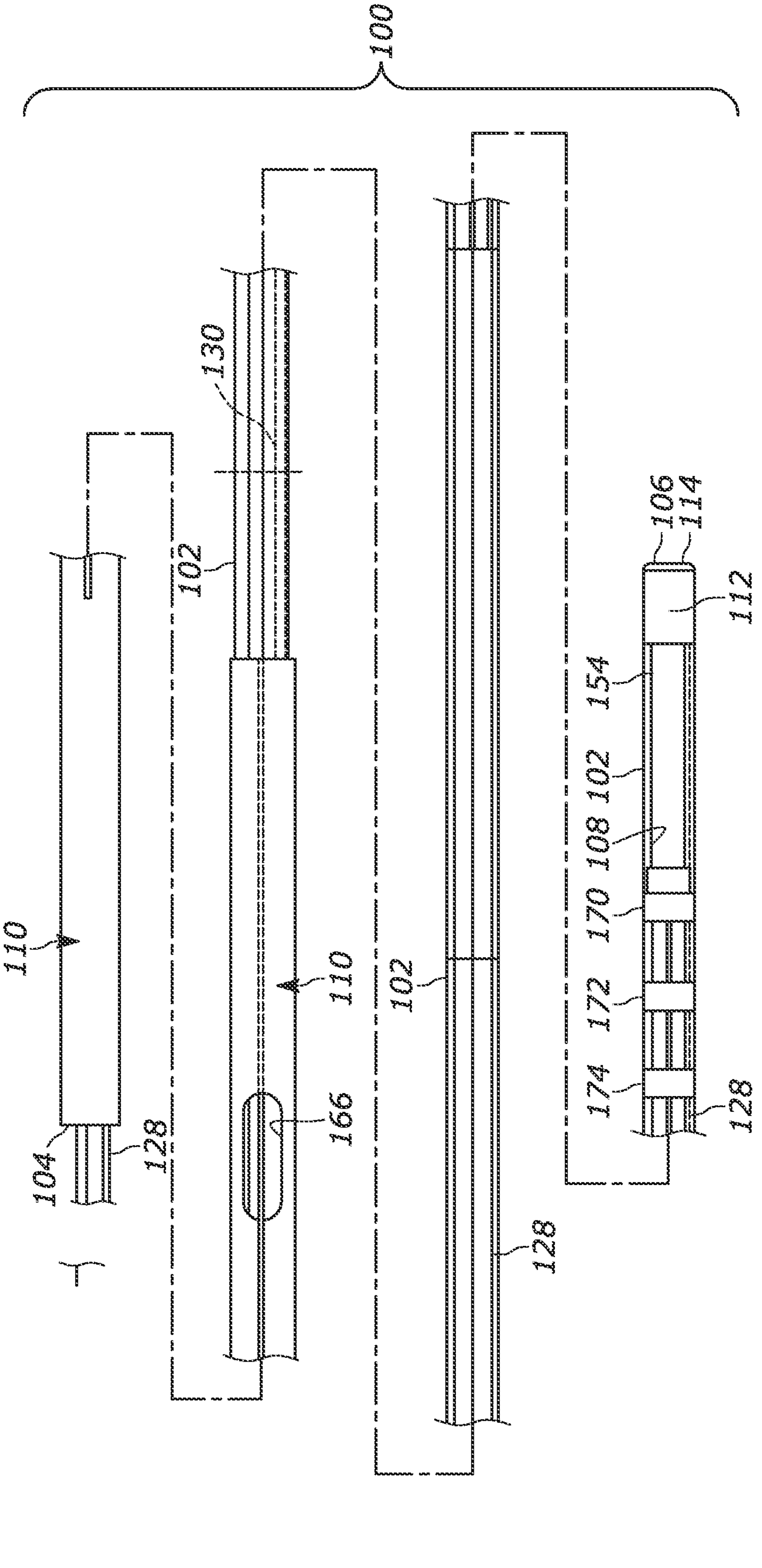
FIG. 1 is an assembly view of an example integrated imaging-ablation catheter.

An integrated imaging-ablation catheter includes an optical imaging probe and an ablation electrode. For example, the imaging probe is an optical coherence tomography (OCT) imaging probe. The catheter may also include a temperature sensor (e.g., thermocouple) and one or more electrodes configured for electrogram recording and 3D mapping.

As described herein, the integrated catheter device is configured to mitigate OCT probe back-out and non-uniform rotation distortion (NURD) that might occur during probe scanning and catheter steering. For example, to reduce NURD, the catheter includes a rotation-protect tubing between the OCT probe and the catheter sheath. The tubing may be a flexible material configured to lubricate the surrounding surface of the OCT probe or otherwise reduce friction during rotation and bending. To reduce (or eliminate) back-out of the OCT probe, such as during bending, the catheter includes a position limiting joint to fix a relative position of the rotation-protect tubing with respect to the catheter sheath.

In some examples the OCT probe is configured to implement polarization sensitive OCT (PSOCT), which provides high resolution (e.g., about 10-20 μm) in-depth (e.g., about 1-2 mm) noninvasive real-time imaging. The PSOCT probe thus can provide images and other data to guide RFA in the left atrium as well as to other target sites of patients.

As described herein, the integrated imaging-ablation catheter guidance of PVI in the LA through the use of imaging, including PSOCT. For example, PS OCT (or other) images generated by the imaging probe, which may be combined with other localized measurements (e.g., temperature and/or electrograms), provide direct lesion transmurality feedback to guide PVI procedures and thereby improve its efficacy.

FIGS. 1-6 depict an example of an integrated imaging-ablation catheter 100. The catheter 100 includes an elongate tubular body 102 having spaced apart proximal and distal ends 104 and 106. A lumen 108 extending through the elongate tubular body 102. In some examples sheaths (e.g., hypotubes) and/or coatings may be applied to the outer surface of the tubular body 102, such as hypotube 110 at the proximal end of the catheter 100.

Figure 5:
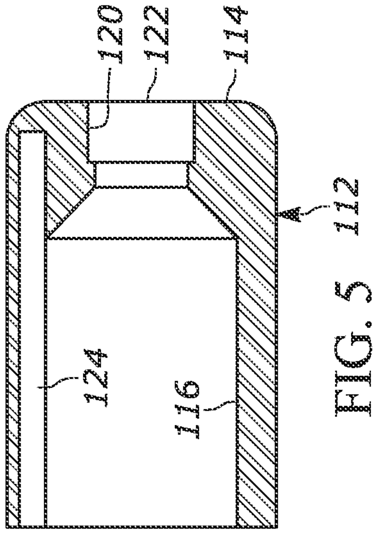
FIG. 5 is cross-sectional view of FIG. 4 taken along line 5-5 showing part of the distal end.
Figure 6:
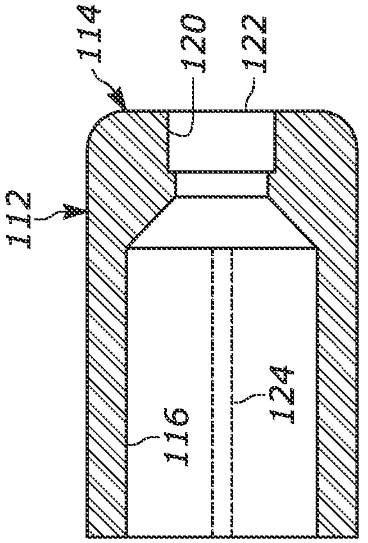
FIG. 6 is cross-sectional view of FIG. 4 taken along line 6-6 showing another part of the distal end.
Figure 4:
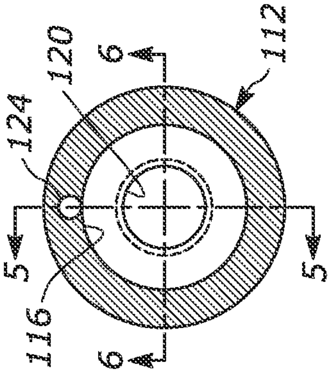
FIG. 4 is a front view of the distal end of the integrated imaging-ablation catheter taken along line 4-4 of FIG. 3.

The catheter 100 includes an ablation electrode 112 extending from the distal end of the elongate tubular body to terminate in a distal end 114 of the catheter. For example, as shown in FIGS. 4, 5 and 6, the ablation electrode 112 includes a central lumen 116 that is dimensioned and configured to accommodate an imaging probe 118. In some examples the ablation electrode is composed of two monopolar electrodes forming a bipolar pair. In some examples, a counter-bore receptacle 120 is formed in the distal end 114 of the ablation electrode 112 to receive a window 122 of an optically transparent material. 118. For example, the window 122 is attached within the receptacle 120 (e.g., using an optical adhesive, swaging, crimping, micromolding, friction, etc.) to protect the 118 probe from blood or other contaminants and allows for optical imaging through the window 122. The material of the window 122 can be a glass or polymer having physical properties to allow light to pass through the window without a large scattering of light. The window 122 is optically transparent at least for a wavelength of light used by the imaging probe. Anti-refraction coatings may be applied on one or both surfaces of the window 122 to enable the improved image quality.

Additionally, the ablation electrode 112 includes another lumen (e.g., a slot) 124 formed in the sidewall of the ablation electrode spaced radially apart from and parallel to the larger center lumen 116. The lumen 124 has a diameter to house a temperature sensor that is located adjacent the ablation electrode distal end 114. For example, the temperature sensor is implemented as a thermocouple (e.g., a type K or other type of thermocouple) is mounted in the lumen 124 adjacent to the ablation electrode distal end 114. A distal end of the lumen 124 can be closed so as to position the temperature sensor nearly at the end but not exposed on the distal end from the outside of the catheter 100. The temperature sensor 126 thus is configured to measure the temperature at tissue surface during ablation of the tissue by the electrode 112. The distal end of temperature sensor may be protected with a coating to ensure desired performance characteristics.

One or more sensor wires (e.g., twisted pair, pigtail conductors) 128 are coupled to the temperature sensor 126 and extend through the catheter 100 to carry electrical signals to and/or from the sensor. For example, the sensor wire 128 may extend through a corresponding lumen 130 of the tubular body 102 of the catheter 100 and out the proximal end 104 of the catheter for connection to a connector of associated circuitry (not shown). The temperature sensor 126 may be mounted adjacent the distal end of the ablation electrode, a conductor coupled with the temperature sensor to carry a temperature signal from the temperature sensor toward the proximal end of the elongate tubular body. As may be understood by those skilled in the art, other sensors (e.g. pressure sensors) or electrodes (e.g. bipolar electrode pairs) may be adapted to be mounted adjacent to the distal end of the ablation catheter in a similar fashion. In some examples the sensor wires may be configured to have a dielectric strength sufficient to withstand DC voltages in excess of 100 V to 1000 V, or 250-750 V, or about 500 V.

Figure 3:
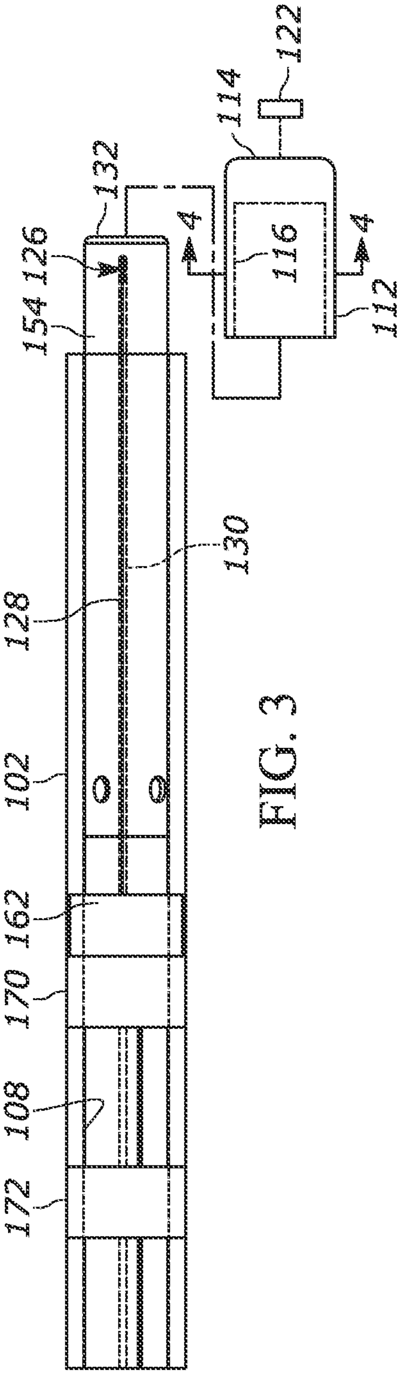
FIG. 3 is an enlarged view of a distal end portion of the integrated imaging-ablation catheter of FIGS. 1 and 2.

An elongate distal hypotube 154 is positioned within and extends through a distal portion of the lumen 108 of the elongate tubular body 102. The distal hypotube 154 terminates in a distal end 132 that is sized and configured to receive the ablation electrode 112 on an outer surface thereof, such as shown in FIG. 3.

Figure 7:
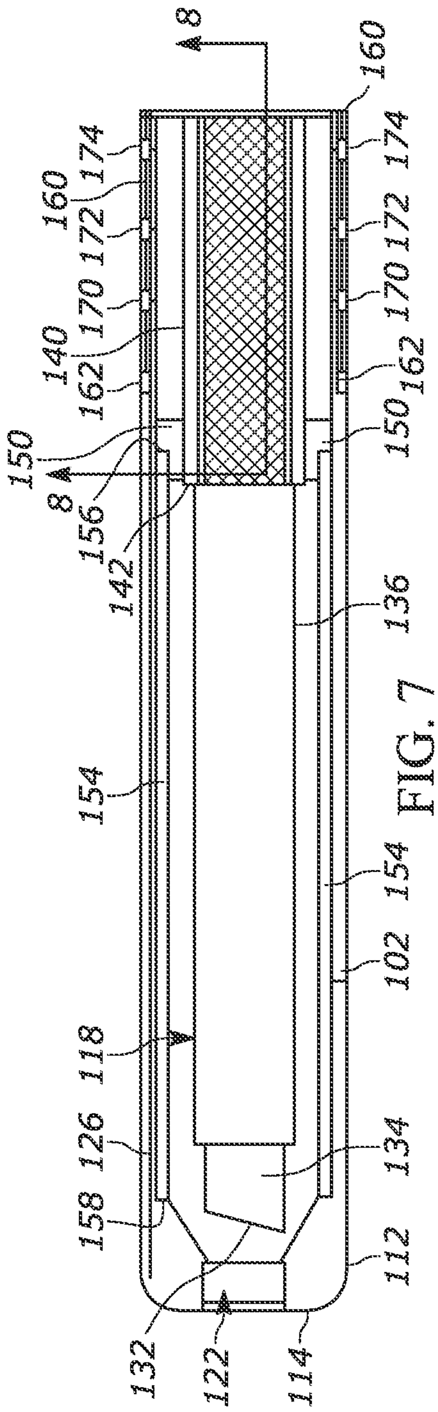
FIG. 7 is a cross-sectional view showing an example of a distal end portion of an integrated imaging-ablation catheter.
Figure 8:
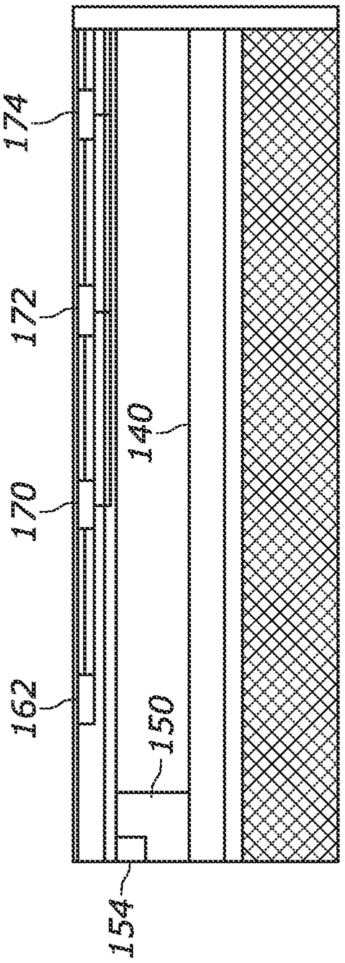
FIG. 8 is an enlarged view of part of the integrated imaging-ablation catheter of FIG. 7.

The imaging probe 118 is mounted within the proximal hypotube 154. The imaging probe 118 is configured to acquire optical images through the window 122 (e.g., through the window. For example, as best shown in the example of FIGS. 7 and 8, the probe 118 includes a lens (e.g., a GRIN lens) 134 at the distal end 132 of the probe to focus light from an optical fiber or other optical waveguide. The probe 118 also may include a hypotube 136 that holds the lens 134 and an optical fiber together within the central lumen 108. For example, the lens 134 is coupled to an optical fiber pigtail using an optical adhesive or other means to attach the lens with the optical fiber (e.g., fused by heat or ultrasonic welding, overmolding, pressing, crimping, swaging, or friction fit).

In an example, the imaging probe 118 is an OCT probe coupled to an OCT scanning system by one or more optical fibers that extend from the probe through the catheter 100. In the catheter 100, the OCT probe may be implemented as a forward scanning probe with its viewing angle aligned to image through the window 122 mounted at the end 114 of the ablation electrode. The scanning system includes a controller and a light source configured to send a laser beam through the probe and onto an object (e.g., tissue). The OCT probe collects back-reflected light that is sent through an optical fiber, extending through the probe and catheter 100, to the optical scanning system. The scanning system is configured to generate an OCT image based on the back-reflected light. The probe 118 may be rotated about its central longitudinal axis during scanning through the window 122. In other examples, the probe may be kept stationary relative to the catheter body 102 during scanning Additionally, because the OCT probe is integrated in the catheter with the ablation electrode 112, the OCT probe 118 may be activated for scanning during ablation, which may involve stationary or rotational scanning to collect images or reflectometry signals of subject tissue.

As one example, the scanning system may be configured to perform polarization sensitive OCT, such as disclosed in U.S. Pat. No. 7,826,059, entitled Method and apparatus for polarization-sensitive optical coherence tomography, which is incorporated herein by reference. Other scanning systems may be used in other examples.

The catheter 100 also includes a flexible tubing 140 extending over a length of the imaging probe 118 and configured to permit at least rotational movement of the probe within the flexible tubing 140. The flexible tubing is further configured to limit the rotation of the imaging probe and to inhibit axial movement of the probe. In an example, a distal end portion 142 of the flexible tubing 140 holds the probe 136 at an axial position relative to the elongate tubular body 102. Additionally, the inner surface of the flexible tubing 140 is configured to hold the probe concentric with the central axis of rotation and thereby reduce NURD during rotation of the probe (e.g., when bending to traverse a curved path). Additionally, the inner surface of the flexible tubing 140 may be implemented to have low friction (e.g., by applying lubricant or other friction reducing coating) to reduce frictional forces during rotation between the probe and inner surface during rotation and bending of the probe 118.

Figure 10:
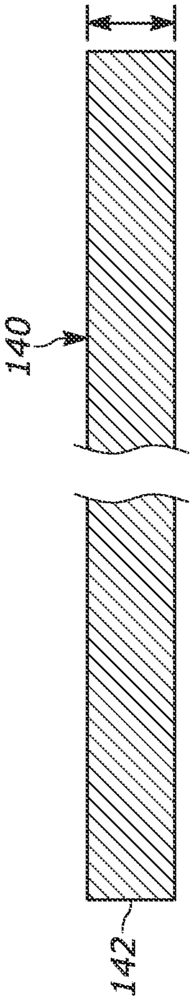
FIGS. 9 and 10 are front and side elevations, respectively, showing an example of flexible tubing that may be used in an integrated imaging-ablation catheter.
Figure 9:
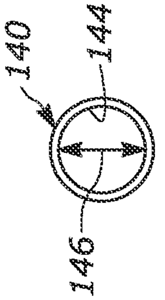

As a further example, with reference to FIGS. 9 and 10, the flexible tubing 140 may include one or more elongate flexible tubes having a low friction inner surface 144. For example, the flexible tubing 140 may include multiple lengths of tubes be arranged end-to-end, which may be connected together or remain free separate lengths of tubing. The flexible tubing 140 has an inner diameter 146 that approximates or is slightly larger than the outer diameter of the hypotube 136 of the probe assembly 118. The flexible tubing permits bending along its central axis but is configured to prevent longitudinal compression or elongation. For example, the flexible tubing 140 can be implemented as a spiral tube or a helical cut hypotube. The flexible tubing 140 can also be formed of a coil. The flexible tubing 140 may be formed of any known metal, e.g. stainless steel or nitinol. In other examples, the flexible tubing may be implemented from various materials, such as polyetheretherketone (PEEK) tubing, polyimide tubing, polytetrafluoroethylene (PTFE) tubing, PEEK-coated spiral tubing, polyimide-coated spiral tubing, and PTFE-coated spiral tubing or helical cut hypotube.

As shown in the examples of FIGS. 7 and 8, the catheter 100 includes a joint 150 to couple an outer surface of the distal end portion 142 of the flexible tubing 140 to the elongate tubular body 102. The joint is configured to maintain the flexible tubing coaxially within the lumen of the catheter 100 as to mitigate radial movement of the OCT probe relative to the elongate tubular body. As shown, the joint 150 is placed between the outer surface of the flexible tubing 140 and the inner surfaces of the tubular body 102 and an elongated electrode hypotube 154. The electrode hypotube 154 is mounted within the distal end portion of the tubular body 102. The electrode hypotube 154 has proximal and distal ends 156 and 158 and circumscribes the imaging probe 118, such as shown. In an example, the proximal end 156 of the electrode hypotube 154 abuts the joint 150.

As a further example the joint 150 is in the form of a single ring that circumscribes the distal end of the flexible tubing. In another example, the joint includes a plurality of joint portions spaced axially apart distributed along the circumference of the flexible tubing 140. The joint 150 thus is configured to stabilize (e.g., maintain or fix) the relative distance of between the end 132 of the probe 118 and the inner surface of the window 122. For example, the distance between the distal end 132 (the lens 134) and the window 122 may be set to provide a desired fixed imaging distance from the probe to the subject tissue. In one example, the joint comprises an adhesive to hold the distal end 142 of the flexible tubing 140 at a fixed axial position within the hypotube 154 and body 102. Other type of joints can be used in other examples, including a heat joint, friction fit joint, crimp joint, swage, threading, weld, or any other joint to stabilize the axial position of the probe 118, as described herein.

Figure 2:
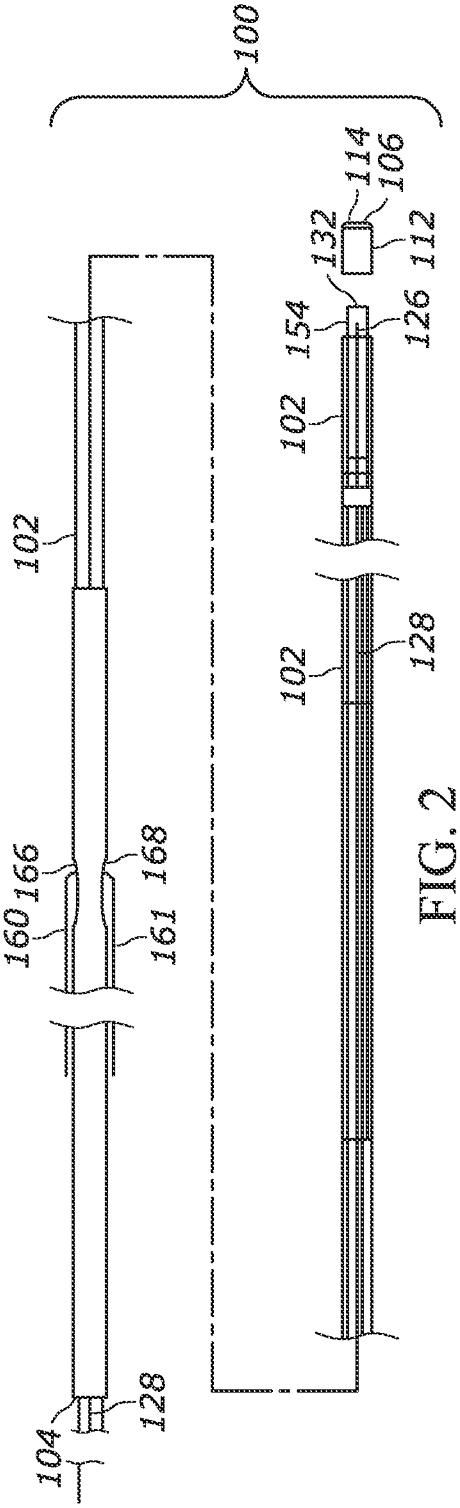
FIG. 2 is an assembly view of the integrated imaging-ablation catheter of FIG. 1 rotated about 90 degrees about its longitudinal axis.

The catheter 100 also may include steering cables 160, 161 having distal ends coupled (e.g., welded or otherwise coupled) to a steering cable anchor (e.g., a ring structure) 162 that is fixed along a circumferential outside surface of the distal end of catheter body 102. For example, the steering cables 160, 161 may extend through the tubular body 102 within respective channels on diametrically opposed sides of the catheter sheath and be attached to the anchor 162. In some examples steering cables 160 and 161 connect to the distal most end 114 of the catheter 100. Other ends of the cables may extend through respective channels and exit the body 102 through apertures 166, 168 formed in the tubular body 102, as shown in FIGS. 1 and 2. For example, a user may pull the cables 160, 161 to effect steering of the catheter 100.

In some examples, the catheter 100 also includes one or more electrodes 170, 172 and 174 mounted on a radially outer surface of the body portion 102. In the example of FIGS. 1, 2, 3, 6 and 7, the catheter 100 has three electrodes (e.g., configured as ring electrodes) distributed in a spaced apart arrangement along the distal end portion. The electrodes may be ring electrodes that circumscribe the body 102, such as configured as mapping electrodes to sense electrograms or other electrophysiological signals. There can be any number of one or more such electrodes along the catheter body, which may be ring or other shaped electrodes (e.g., rectangular, circular, etc.).

In some examples, the electrodes 170, 172 and 174 may also be configured to form bipolar pairs amongst one another and/or the ablation electrode 112. Such bipolar pairs may be configured to deliver RF electricity or high voltage electrical pulses, such as those utilized in irreversible electroporation (IEP). In one example of IEP with bipolar pairs of electrodes, monophasic electrical impulses are employed. In another example of IEP with bipolar pairs of electrodes, biphasic electrical impulses are employed. In an example of IEP employing biphasic electrical impulses there are 1-6 pulse trains consisting of 10-60 pulses. Such pulse trains may be delivered over 1-6 seconds at frequencies of 1 Hz and may have amplitudes of 200-700 V and current range of 8-25 Amps.

As a further example, the thickness (e.g., 2 mm versus 4 mm) and/or character (e.g. fat versus muscle) of the tissue to be ablated may be evaluated via OCT, and the energy to be delivered titrated appropriately. In an example of OCT guided IEP, 2 mm-4 mm thick muscle or another target site having desired tissue characteristics is identified optically based on OCT image data acquired via the OCT probe. Responsive to the OCT data, the voltage, number of pulses, and/or pulse width can be titrated to deliver the desired current density to create a transmural lesion while reducing excessive heat generation. In another example of OCT guided IEP, 2 mm-4 mm thick muscle (or a site having other desired tissue characteristics) is targeted for ablation and the voltage, number of pulses, or pulse width is automatically adjusted in real time as the lesion depth increases (one or more of the parameters is reduced as lesion depth increases). In another example of OCT guided IEP, fatty tissue is identified optically and targeted for ablation by reducing the duration of pulses (e.g. 1 nanosecond-200 microseconds). In a related example both OCT and impedance measurements may be used to titrate electrical energy during ablation.

As described herein, the integrated imaging-ablation catheter 100 thus is configured to perform a variety of functions. For example, the catheter 100 can accurately record electrograms, determine 3D catheter location, monitor temperature change, as well as directly guide catheter-tissue apposition and monitor lesion formation in the LA (or other locations) directly in real-time.

Figure 11:
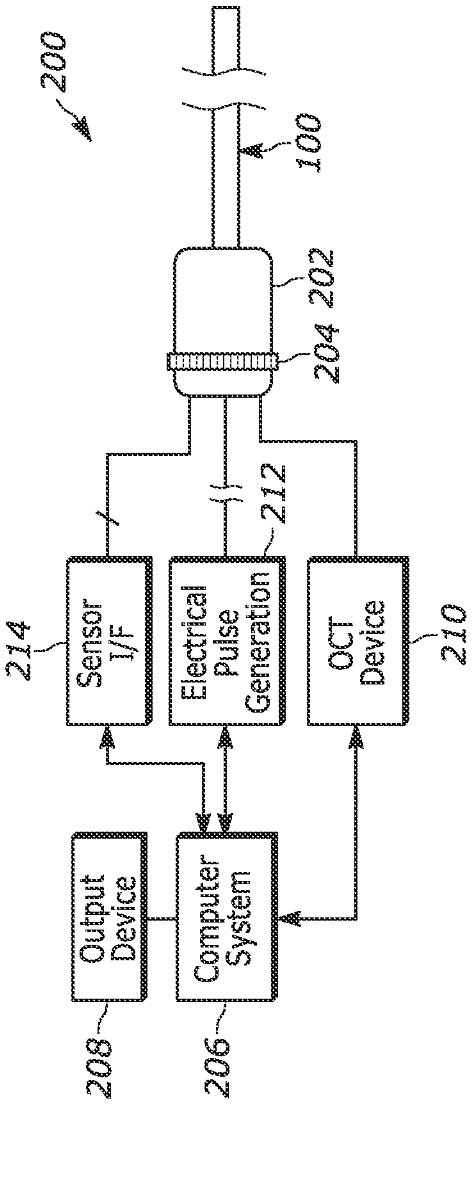
FIG. 11 depicts an example of an ablation and imaging control system.

FIG. 11 depicts an example ablation and imaging system 200 implementing the catheter 100. The catheter can be implementing according to the examples described here. Accordingly, the description of FIG. 11 also refers to FIGS. 1-10.

The system 200 includes hardware and software arranged and configured to control the ablation catheter 100 and to generate images as described herein. In the example of FIG.

11, the catheter 100 is shown to include a handle 202 from which the elongate body extends. The handle 202 can also be implemented as a control handle having one or more knobs (or other control mechanisms) 204 configured to adjust the length of respective pull wires for steering the distal end portion of the catheter. For example, rotating the knob 204 in one direction cause deflection of the distal end portion in a first direction and rotating the knob in another direction causes deflection in another opposite direction.

The system 200 also can include a computing system 206 to which one or more output devices 208 can be coupled. For example, the output device 208 can include a display, such as configured to display images acquired by an imaging probe (e.g., OCT imaging probe) that is implemented in the catheter 100. For example, the one or more OCT images can be displayed on the output device 208, such as generated by an OCT device 210.

The OCT device 210 can include a light source and an arrangement of optical components to send incident light and detect scattered and reflected light from an object (e.g., in vivo or in vitro). The OCT device 210 can supply OCT data to the computer system 206, which can construct one or more respective images (e.g., two-dimensional or three-dimensional images) of the object based on the OCT data, which can be displayed on output device 208. Examples of apparatus that can be used to implement the OCT device 210, including polarization sensitive OCT devices, are disclosed in U.S. Pat. Nos. 10,591,275 and 7,826,059 and 6,615,072, each of which is incorporated herein by reference.

The computer system 206 can include a processor (and/or the OCT device 210 can include a processor) programmed to perform interferometry and calculations on the detector signal and compute optical polarization properties of the sample that is illuminated. The processor can also compute other optical properties such as total reflective power, B polarization, net retardance or net extinction ratio based on processing of the OCT signals. The computer system can utilize the computations a corresponding OCT images that can be presented on the display and/or stored in memory.

The system 200 can also include an electrical pulse generator 212 and one or more sensor interfaces 214. For example, the electrical pulse generator 212 can be coupled to the ablation electrode 112 and configured to supply electrical pulses for ablating tissue. For example, the computer system 206 can provide instructions to the electrical pulse generator 212 to control application of ablative to the electrode 122 for ablating tissue, such as by configuring one or more parameters (e.g., frequency and power) of energy being applied. The OCT device 210 can acquire OCT data (e.g., before during and after the ablation) and the computer system can generate corresponding OCT images displayed in real-time or near real-time. The OCT images can be used to control the ablation (e.g., by setting respective parameters of the pulse generator 212) automatically or in response to a user input based on the OCT images that are generated. Thus, as described herein, the system 200, including the catheter 100 having an integrated OCT probe, can be used to produce OCT images and other information to help guide and monitor the RFA procedure in real-time, including direct monitoring of changes in tissue responsive to the ablation.

The computer system 206 can be configured to provide other information (e.g., text or graphical information) to the output device 210, which can also be used to guide the ablation. For example, the computer system 206 can output information to the device 210 representative of operating parameters of the ablation catheter 100 and/or other features sensed by one or more sensors of the catheter 100. For example, as described herein, the catheter can include a temperature sensor 126 and/or one or more sensing electrodes 162, 170, 172, 174. Each sensor can be coupled to the sensor interface 214, which can provide respective sensor data to the computer system 206. The computer system 206 can display information in the form of text and/or graphics on the output device 208 representative of the sensed condition(s). Such sensed information can (along with the OCT images) be used to control the ablation (e.g., by setting respective parameters of the pulse generator 212) automatically or in response to a user input based.

From the above description of the invention, those skilled in the art will perceive improvements, changes and modifications. Such improvements, changes and modifications within the skill of the art are intended to be covered by this application, including the appended claims. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements.

Also, as used herein, the term "couple" or "couples" means either an indirect or direct connection. Thus, if a first device couples to a second device, that connection may be through a direct connection or through an indirect connection via other devices and connections. For example, if device A generates a signal to control device B to perform an action, in a first example device A is coupled to device B, or in a second example device A is coupled to device B through intervening component C if intervening component C does not substantially alter the functional relationship between device A and device B such that device B is controlled by device A via the control signal generated by device A.

Furthermore, a circuit or device that is said to include certain components may instead be configured to couple to those components to form the described circuitry or device. For example, a structure described as including one or more elements A, B and C may instead include only the A elements within a single physical device and may be configured to couple to at least some of the elements B and/or C to form the described structure, either at a time of manufacture or after a time of manufacture, for example, by an end-user and/or a third-party.

As used herein, the term "includes" means includes but not limited to, the term "including" means including but not limited to. The term "based on" means based at least in part on. All references, publications, and patents cited in the present application are herein incorporated by reference in their entirety.

What is claimed is:

1. An ablation catheter, comprising:

an elongate tubular body having spaced apart proximal and distal ends and a lumen extending through the elongate tubular body;

an ablation electrode extending from the distal end of the elongate tubular body to terminate in a respective distal end of the ablation electrode;

an optical imaging probe having an elongate body portion, the elongate body portion extending from the proximal end of the elongate tubular body through the lumen of the elongate tubular body and terminating in a distal end that is spaced a distance from the distal end of the ablation electrode; and a flexible tubing extending over a proximal portion of the elongate body portion of the optical imaging probe and configured to permit rotational movement of the optical imaging probe within and relative to the flexible tubing, a distal end portion of the flexible tubing being spaced proximally from the distal end of the elongate body portion of the optical imaging probe; and a joint circumscribing the distal end portion of the flexible tubing and spacing apart an outer surface of the flexible tubing and an inner surface of the elongate tubular body, the joint being configured to couple the outer surface of the distal end portion of the flexible tubing to the elongate tubular body to hold the distal end portion of the flexible tubing at an axial position relative to the elongate tubular body and thereby fix an axial distance between the distal end of the optical imaging probe and the distal end of the ablation electrode.

2. The catheter of claim 1, wherein the joint comprises one of an adhesive, a heat joint, a friction-fit joint, a crimp joint, a swage, threading, and a weld.

3. The catheter of claim 1, wherein the flexible tubing comprises one or more elongate flexible tubings having a low friction inner surface.

4. The catheter of claim 1, wherein the flexible tubing comprises a spiral tube or a helical cut hypotube.

5. The catheter of claim 1, further comprising an elongate hypotube for the ablation electrode having proximal and distal ends and circumscribing a distal portion of the elongate body portion of the optical imaging probe, the elongate hypotube for the ablation electrode mounted within the elongate tubular body so that the proximal end of the elongate hypotube abuts the joint, and the optical imaging probe located within the elongate hypotube for the ablation electrode as to permit rotation but prevent axial movement of the elongate body portion of the optical imaging probe within the ablation catheter.

6. The catheter of claim 1, wherein the distal end of the ablation electrode comprises a central aperture extending therethrough, wherein the optical imaging probe comprises a forward scanning probe aligned to image through the central aperture of the ablation electrode.

7. The catheter of claim 6, wherein the optical imaging probe is an optical coherence tomography (OCT) probe.

8. The catheter of claim 7, wherein the OCT probe is a polarization sensitive OCT probe.

9. The catheter of claim 6, further comprising a window within the central aperture, an outer surface of the window including an optically transparent material, and the outer surface of the window being inset proximally from a distal edge of the ablation electrode.

10. The catheter of claim 1, further comprising a temperature sensor mounted adjacent the distal end of the ablation electrode, a conductor coupled with the temperature sensor to carry a temperature signal from the temperature sensor toward the proximal end of the elongate tubular body.

11. The catheter of claim 10, further comprising a longitudinal slot formed in the distal end portion of the ablation electrode, the temperature sensor being mounted in the longitudinal slot.

12. The catheter of claim 10, further comprising a pressure sensor mounted adjacent the distal end of the ablation electrode.

13. The catheter of claim 1, where the ablation electrode includes one or more bipolar electrode pairs.

14. A system comprising:

a catheter comprising:

an elongate tubular body having spaced apart proximal and distal ends and a lumen extending through the elongate tubular body;

an ablation electrode extending from the distal end of the elongate tubular body to terminate in a respective distal end of the ablation electrode;

an optical imaging probe having an elongate body portion, the elongate body portion of the optical imaging probe extending from the proximal end of the elongate tubular body through the lumen of the elongate tubular body and terminating in a distal end thereof that is spaced proximally a distance from the distal end of the ablation electrode;

a flexible tubing extending over a proximal portion of the elongate body portion of the optical imaging probe and configured to permit at least rotational movement of the probe within and relative to the flexible tubing and the elongate tubular body, a distal end portion of the flexible tubing being spaced proximally from the distal end of the elongate body portion of the optical imaging probe; and a joint circumscribing the distal end portion of the flexible tubing and spacing apart an outer surface of the flexible tubing and an inner surface of the elongate tubular body, the joint being configured to couple the outer surface of the distal end portion of the flexible tubing to the elongate tubular body and hold the distal end portion of the flexible tubing at an axial position relative to the elongate tubular body to fix an axial distance between the distal end of the optical imaging probe and the distal end of the ablation electrode;

a pulse generator; and a controller configured to control the pulse generator to supply electrical energy to the ablation electrode to implement ablation.

15. The system of claim 14, wherein the distal end of the ablation electrode comprises a central aperture extending therethrough, wherein the optical imaging probe comprises a forward scanning probe aligned to image through the central aperture of the ablation electrode.

16. The system of claim 15, wherein the optical imaging probe is an optical coherence tomography (OCT) probe.

17. The system of claim 16, wherein the OCT probe is a polarization sensitive OCT probe.

18. The system of claim 15, further comprising a window within the central aperture, an outer surface of the window including an optically transparent material, and the outer surface of the window being inset proximally from a distal edge of the ablation electrode.

19. The system of claim 14, further comprising a temperature sensor mounted adjacent the distal end of the ablation electrode, a conductor coupled with the temperature sensor to carry a temperature signal from the temperature sensor toward the proximal end of the elongate tubular body.

20. The system of claim 19, further comprising a longitudinal slot formed in the distal end portion of the ablation electrode, the temperature sensor being mounted in the longitudinal slot.

21. The system of claim 19, further comprising a pressure sensor mounted adjacent the distal end of the ablation electrode.

22. An ablation catheter, comprising:

an elongate tubular body having spaced apart proximal and distal ends and a lumen extending through the elongate tubular body;

an ablation electrode extending from the distal end of the elongate tubular body to terminate in a respective distal end of the ablation electrode;

an optical imaging probe having an elongate body portion, the elongate body portion extending from the proximal end of the elongate tubular body through the lumen of the elongate tubular body and terminating in a distal end that is spaced a distance from the distal end of the ablation electrode;

a flexible tubing extending over a proximal portion of the elongate body portion of the optical imaging probe and configured to permit rotational movement of the optical imaging probe within and relative to the flexible tubing, a distal end portion of the flexible tubing being spaced proximally from the distal end of the elongate body portion of the optical imaging probe, and the distal end portion of the flexible tubing being configured to hold the elongate body portion of the optical imaging probe and mitigate axial movement of the optical imaging probe relative to the elongate tubular body and thereby stabilize a distance of between the distal end of the elongate body portion of the optical imaging probe and the respective distal end of the ablation electrode; and a joint circumscribing the distal end portion of the flexible tubing and coupled between an outer surface of the distal end portion of the flexible tubing to an inner surface of the elongate tubular body, the joint configured to space the outer surface of the flexible tubing radially inwardly from the inner surface of the elongate tubular body and maintain the flexible tubing coaxially within the lumen, the joint configured to hold the distal end portion of the flexible tubing at an axial position relative to the elongate tubular body to fix an axial distance between the distal end of the optical imaging probe and the distal end of the ablation electrode, and the outer surface of the flexible tubing that extends through the lumen proximally from the joint being spaced apart from the inner surface the elongate tubular body.

* * * * *